United States Patent
Sung et al.

(10) Patent No.: US 9,414,788 B2
(45) Date of Patent: Aug. 16, 2016

(54) X-RAY IMAGING APPARATUS AND METHOD OF GENERATING STEREOSCOPIC IMAGE

(71) Applicant: SAMSUNG ELECTRONICS CO., LTD., Suwon-si (KR)

(72) Inventors: Young Hun Sung, Hwaseong-si (KR); Kang Eui Lee, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 132 days.

(21) Appl. No.: 14/105,455

(22) Filed: Dec. 13, 2013

(65) Prior Publication Data
US 2014/0185750 A1 Jul. 3, 2014

(30) Foreign Application Priority Data
Dec. 28, 2012 (KR) .................. 10-2012-0156348

(51) Int. Cl.
*A61B 6/02* (2006.01)
*G01N 23/04* (2006.01)
*A61B 6/00* (2006.01)

(52) U.S. Cl.
CPC ............... *A61B 6/022* (2013.01); *A61B 6/4007* (2013.01); *A61B 6/482* (2013.01); *A61B 6/502* (2013.01); *A61B 6/5235* (2013.01); *G01N 23/04* (2013.01); *A61B 6/4405* (2013.01); *G01N 2223/414* (2013.01)

(58) Field of Classification Search
CPC ...... A61B 6/022; A61B 6/4007; A61B 6/502; A61B 6/503; A61B 6/504; A61B 6/52; A61B 6/5205; A61B 6/5211; A61B 6/5258
See application file for complete search history.

(56) References Cited

U.S. PATENT DOCUMENTS

| | | | |
|---|---|---|---|
| 9,149,239 B2 * | 10/2015 | Lee | A61B 6/022 |
| 2006/0074287 A1 | 4/2006 | Neumann et al. | |
| 2006/0104406 A1 | 5/2006 | Siltanen et al. | |
| 2009/0238334 A1 * | 9/2009 | Brahme | A61B 6/022 378/41 |
| 2009/0257551 A1 * | 10/2009 | Dafni | A61B 6/022 378/6 |
| 2010/0208865 A1 * | 8/2010 | Sendai | 378/28 |
| 2010/0249647 A1 * | 9/2010 | Nakayama | 600/567 |
| 2010/0278301 A1 | 11/2010 | Kano | |
| 2011/0026667 A1 | 2/2011 | Poorter | |
| 2013/0300737 A1 * | 11/2013 | Nishino et al. | 345/419 |
| 2014/0112430 A1 * | 4/2014 | Lee | A61B 6/022 378/4 |
| 2014/0161341 A1 * | 6/2014 | Ohta | A61B 6/022 382/132 |
| 2014/0185750 A1 * | 7/2014 | Sung et al. | 378/41 |
| 2015/0063537 A1 * | 3/2015 | Lee et al. | 378/41 |

FOREIGN PATENT DOCUMENTS

| | | | |
|---|---|---|---|
| KR | 10-2012-0025653 A | | 3/2012 |
| WO | WO 2012039121 A1 * | | 3/2012 |

* cited by examiner

*Primary Examiner* — Thomas R Artman
(74) *Attorney, Agent, or Firm* — Sughrue Mion, PLLC (57) ABSTRACT

Disclosed herein are an X-ray imaging apparatus and a method for generating a stereoscopic image by using the apparatus. The stereoscopic image generation method includes emitting first X-rays toward a target object at a first emission angle, detecting the first X-rays which have propagated through the target object in order to acquire a first X-ray image, emitting second X-rays toward the target object at a second emission angle which is different from the first emission angle, detecting the second X-rays which have propagated through the target object in order to acquire at least a second X-ray image, and generating a stereoscopic image based on the first X-ray image and the at least second X-ray image.

19 Claims, 11 Drawing Sheets

X-RAY IMAGING APPARATUS AND METHOD OF GENERATING STEREOSCOPIC IMAGE

CROSS-REFERENCE TO RELATED APPLICATION(S)

This application claims priority from Korean Patent Application No. 10-2012-0156348, filed on Dec. 28, 2012 in the Korean Intellectual Property Office, the disclosure of which is incorporated herein by reference in its entirety.

BACKGROUND

1. Field

Exemplary embodiments relate to an X-ray imaging apparatus and a method for displaying an X-ray image on a screen of a user.

2. Description of the Related Art

An X-ray imaging system irradiates a target object, for example, the human body or various things, supported by an X-ray detector or the like, with X-rays in order to acquire an X-ray image, and displays the acquired X-ray image to a user by using a display device, such as a monitor, such that the user may check and diagnose inner parts of the target object.

Such an X-ray imaging apparatus uses characteristics whereby X-rays are absorbed by or pass through a material according to the characteristics thereof when emitted. An operation of the X-ray image apparatus will now be described. When a voltage is applied in order to accelerate electrons, the electrons are decelerated by Coulombic force around an atomic nucleus in order to emit X-rays according to the principle of conservation of energy. In this case, when a target object is irradiated by the emitted X-rays, the X-rays are absorbed by or propagate through the target object based on the characteristics of a material which constitutes the target object. The X-rays which have propagated through the target object are received and converted into electrical signals in order to acquire an X-ray image. Then, the X-ray image is displayed on a monitor or the like of a user such that the user may check an inner structure of the target object by using the X-rays.

An example of an X-ray imaging apparatus may include a full field digital mammography (FFDM) apparatus. The FFDM apparatus is a medical imaging system which uses X-rays for detection of lesions, such as cancerous tissues, inside the breasts of a woman. By virtue of development of the FFDM apparatus, a breast cancer test may be efficiently performed with respect to women, and a much greater number of cases may be checked than by conventional film type mammography.

In order to acquire an X-ray image by using such an FFDM apparatus, a target object, that is, a breast, is positioned on a detector which has a flat upper surface and is compressed by a compressor in order to increase a surface area toward which X-rays are emitted. In addition, the target object is irradiated by X-rays which are emitted from above the target object, and X-rays which have propagated through the target object are detected in order to generate a flat X-ray image of the compressed target object, that is, the compressed breast. However, in this case, there is a limit in detecting all tissues, in particular, all lesions inside the target object due to high density or overlap of inner tissues.

SUMMARY

Therefore, it is an aspect of one or more exemplary embodiments to provide an X-ray imaging apparatus that enables a user to easily detect tissues, such as, for example, lesions which are hidden by other overlapping tissues due to high density thereof, and to obtain information which relates to a depth at which inner tissues of the target object are present.

In particular, a three-dimensional (3D) stereoscopic image, instead of a simple two-dimensional (2D) image, is generated and provided to a user, such as, for example, a doctor or a diagnostician, such that the user may easily and accurately detect and recognize a target object or tissues inside the target object by using the stereoscopic image.

As a result, the efficiency and accuracy of various image diagnosis processes which involve the use of an X-ray diagnosis apparatus, a mammography apparatus, or the like may be increased.

Therefore, it is an aspect of one or more exemplary embodiments to provide an X-ray imaging apparatus and a method for generating a stereoscopic image by using the apparatus.

Additional aspects of the exemplary embodiments will be set forth in part in the description which follows and, in part, will be obvious from the description, or may be learned by practice of the exemplary embodiments.

In accordance with an aspect of one or more exemplary embodiments, an X-ray imaging apparatus includes a first X-ray generator which is configured to emit first X-rays toward a target object at a first emission angle, at least a second X-ray generator which is configured to emit second X-rays toward the target object at a second emission angle which is different from the first emission angle, a detector which is configured to detect the first X-rays and the second X-rays which have propagated through the target object, an image processor which is configured to acquire a first X-ray image from the detected first X-rays and to acquire at least a second X-ray image from the detected second X-rays, and to generate a stereoscopic image by using the acquired first X-ray image and the acquired at least second image, and a display which is configured to display the generated stereoscopic image. In addition, the X-ray imaging apparatus may further include a basic image controller which is configured to display the first X-ray image on a first screen and to display the second X-ray image on a second screen.

The second X-rays may be emitted at a lower dosage level than a dosage level at which the first X-rays are emitted, and a difference angle δ between the first emission angle and the second emission angle may satisfy $0<\delta\leq 10°$.

The image processor may be further configured to match an image quality of the first X-ray image with an image quality of the at least second X-ray image prior to generating the stereoscopic image.

In accordance with another aspect of one or more exemplary embodiments, an X-ray imaging apparatus includes a first X-ray generator which is configured to emit first X-rays toward a target object at a first emission angle, at least a second X-ray generator which is configured to emit second X-rays toward the target object at a second emission angle which is different from the first emission angle, a detector which is configured to detect the first X-rays and the second X-rays which have propagated through the target object, an image processor which is configured to acquire a first X-ray image from the detected first X-rays and to acquire at least a second X-ray image from the detected second X-rays, and a display apparatus which includes a first display which is configured to display the acquired first X-ray image, a second display which is configured to display the acquired second X-ray image, and a third display which is configured to receive light beams which respectively correspond to the first and second X-ray images and to display a stereoscopic image which is based on the first X-ray image and the second X-ray image and which is generated by using a half mirror method.

In accordance with another aspect of one or more exemplary embodiments, an X-ray imaging apparatus includes an X-ray generator which is configured to emit first X-rays toward a target object at a first emission angle and to emit second X-rays toward the target object at a second emission angle which is different from the first emission angle, a detector which is configured to detect the first X-rays and the second X-rays which have propagated through the target object, and an image processor which is configured to acquire a first X-ray image from the detected first X-rays and to acquire at least a second X-ray image from the detected second X-rays and to generate a stereoscopic image by using the acquired first X-ray image and the acquired at least second image.

In accordance with another aspect of one or more exemplary embodiments, a method for generating a stereoscopic image by using an X-ray imaging apparatus includes emitting first X-rays toward a target object at a first emission angle, detecting the first X-rays which have propagated through the target object in order to acquire a first X-ray image, emitting second X-rays toward the target object at a second emission angle which is different from the first emission angle, detecting the second X-rays which have propagated through the target object in order to acquire at least a second X-ray image, and generating a stereoscopic image by using the first X-ray image and the at least second X-ray image. The method may further include matching an image quality of the first X-ray image with an image quality of the at least second X-ray image prior to the generating the stereoscopic image. The method may further include simultaneously displaying the first X-ray image, the at least second X-ray image, and the stereoscopic image.

Similarly, the second X-rays may be emitted at a lower dosage level than a dosage level at which the first X-rays are emitted. A difference angle δ between the first emission angle and the second emission angle may satisfy 0<δ≤10°.

BRIEF DESCRIPTION OF THE DRAWINGS

These and/or other aspects will become apparent and more readily appreciated from the following description of the exemplary embodiments, taken in conjunction with the accompanying drawings of which.

DETAILED DESCRIPTION

In order to describe the exemplary embodiments with reference to FIGS. 1 to 11, an overall concept of an X-ray imaging apparatus according to an exemplary embodiment will be described with reference to FIG. 1. An X-ray imaging apparatus according to an exemplary embodiment will be described with reference to FIGS. 2 to 9. Lastly, a method for generating a stereoscopic image according to an exemplary embodiment will be described with reference to FIGS. 10 and 11.

Hereinafter, an overall concept of an X-ray imaging apparatus according to an exemplary embodiment will be described with reference to FIG. 1.

Figure 1:
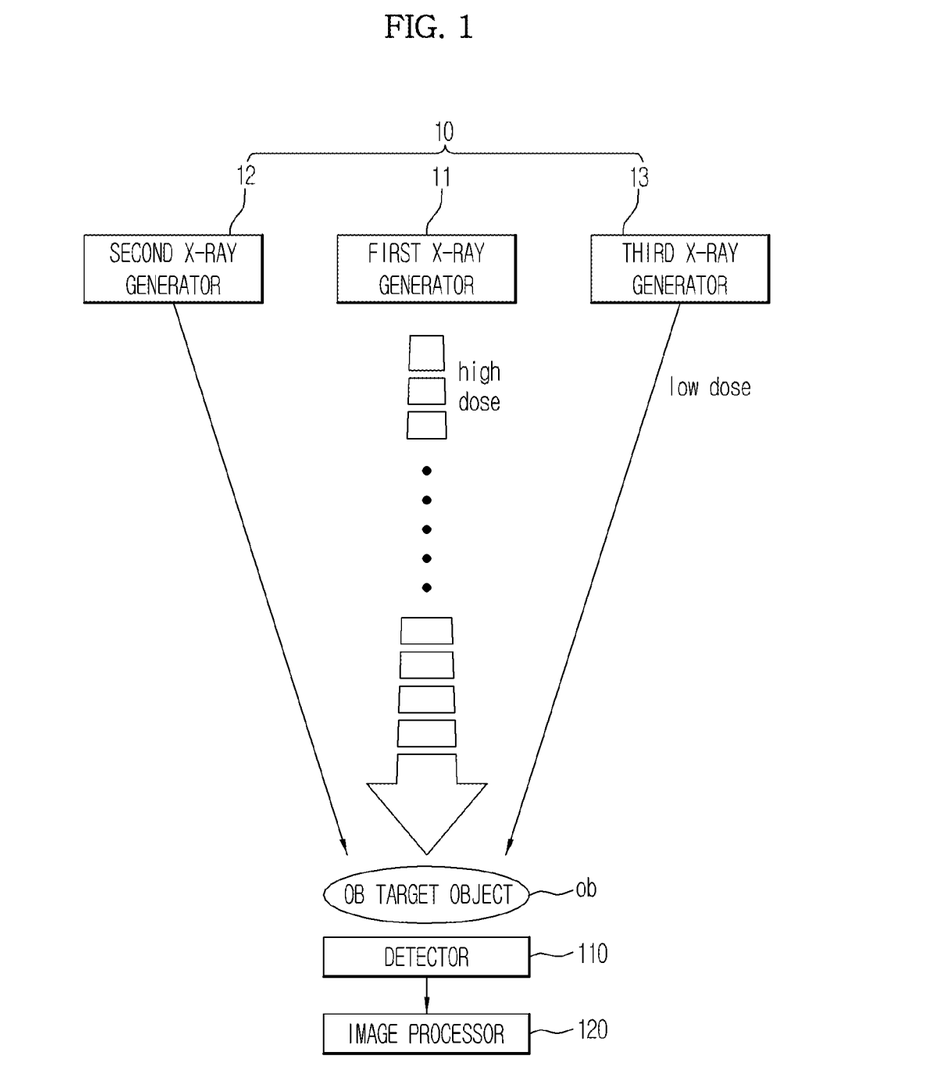
FIG. 1 is a diagram which illustrates an overall concept of an X-ray imaging apparatus, according to an exemplary embodiment.

FIG. 1 is a diagram which illustrates an overall concept of an X-ray imaging apparatus, according to an exemplary embodiment.

Referring to FIG. 1, according to an exemplary embodiment, the X-ray imaging apparatus may include an X-ray generator 10 which is configured to generate X-rays and to irradiate a target object ob with the X-rays, a detector 110 which is configured to detect X-rays which have propagated through the target object ob and to convert the X-rays into electrical signals, and an image processor 120 which is configured to extract and read out X-ray images from the electrical signal which has been converted via the detector 110 and to perform a predetermined image processing process on the X-ray images.

According to an exemplary embodiment, as shown in FIG. 1, the X-ray generator 10 which is configured to generate X-rays includes a first X-ray generator 11 and at least a second X-ray generator, that is, second X-ray generator 12 and third X-ray generator 13. Each of the first, second, and third X-ray generators 11, 12, and 13 irradiates the target object ob with X-rays based on a control which is exercised by a user or a controller. Thus, the X-ray generator 10 sequentially or simultaneously emits X-rays toward the target object ob and the detector 110 a plurality of times.

Then, the detector 110 detects the X-rays which have been emitted by the first X-ray generator 11, the second X-ray generator 12, and the third X-ray generator 13 and which have propagated through the target object ob, and converts and stores the detected X-rays as electrical signals. In addition, the image processor 120 generates a plurality of X-ray images which respectively correspond to X-rays emitted from the first, second, and third X-ray generators 11, 12, and 13, based on the electrical signals.

Thus, the X-ray imaging apparatus may acquire a plurality of X-ray images which are captured with respect to the same target object at different angles via a plurality of X-ray generators, that is, the first, second, and third X-ray generators 11, 12, and 13. In this regard, when imaging angles are within a predetermined range, a plurality of X-ray images may be combined in order to generate a stereoscopic image.

Hereinafter, an X-ray imaging apparatus according to an exemplary embodiment will be described with reference to FIGS. 2 to 9.

Hereinafter, to aid in understanding and for convenience of description, the X-ray imaging apparatus will be described with reference to FIGS. 2 to 9 in terms of a case in which a full field digital mammography (FFDM) apparatus is used as the imaging apparatus. However, the exemplary embodiments are not limited to FFDM. Alternatively, the exemplary embodiments may be applied to X-ray imaging apparatuses used in other fields as well as to medical imaging apparatuses such as FFDM apparatuses. Thus, although the X-ray imaging apparatus will be described in terms of an FFDM, it will be understood that the scope of the exemplary embodiments is not limited to FFDM.

Figure 2:
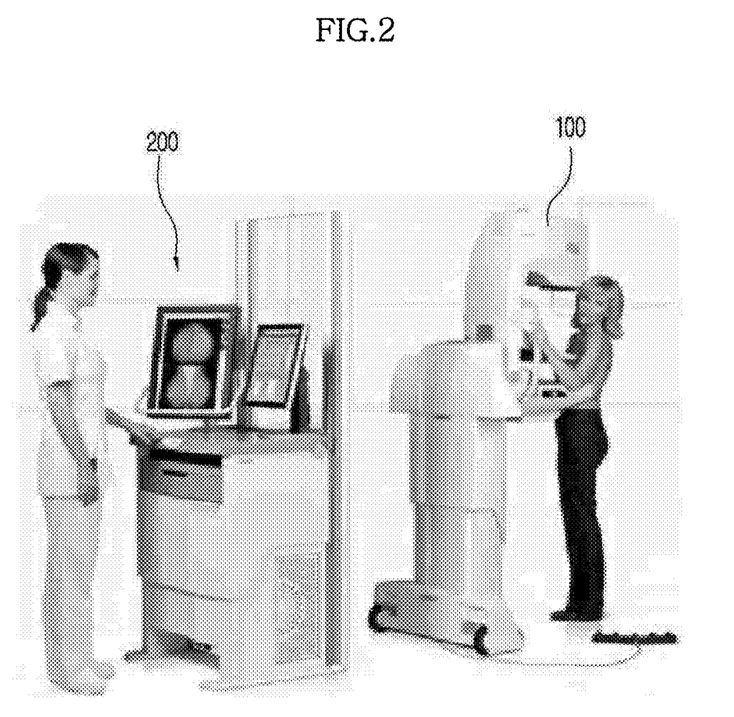
FIG. 2 is an image of an FFDM apparatus as an X-ray imaging apparatus, according to an exemplary embodiment.
Figure 3:
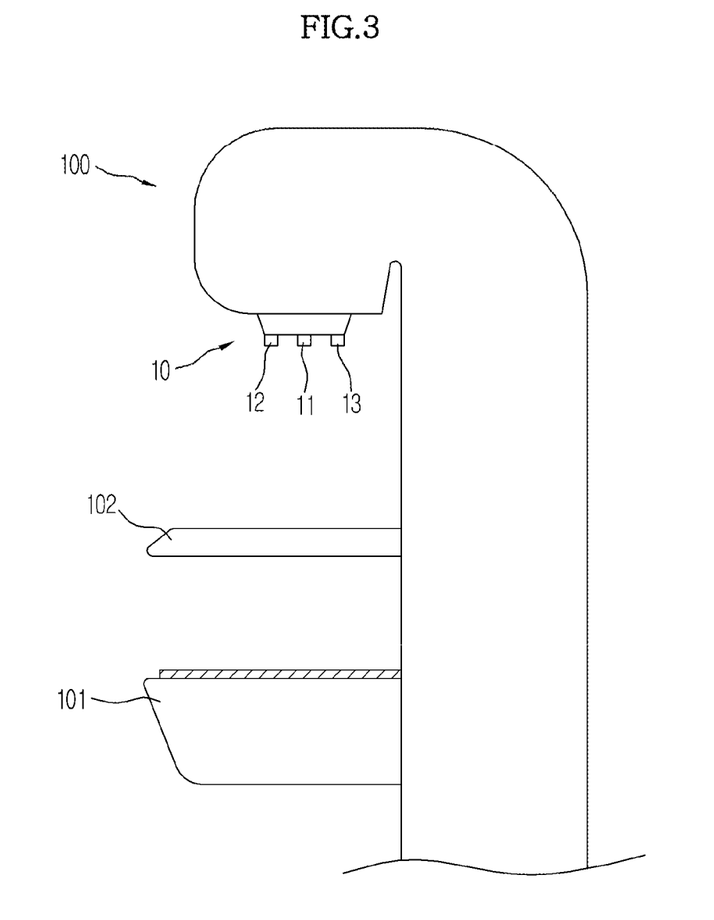
FIG. 3 is a side view of an imaging apparatus of FFDM, according to an exemplary embodiment.

FIG. 2 is an image of an FFDM apparatus as an X-ray imaging apparatus, according to an exemplary embodiment, and FIG. 3 is a side view of an imaging apparatus 100 of FFDM, according to an exemplary embodiment.

As shown in FIG. 2, the FFDM apparatus according to an exemplary embodiment includes the imaging apparatus 100 which is configured to position a target object at a predetermined position, to emit X-rays, and to detect X-rays which have propagated through the target object, and a display apparatus 200 which is configured to display X-ray images to a doctor, a diagnostician, and/or the like.

According to an exemplary embodiment, the imaging apparatus 100 may include the X-ray generators 11, 12, and 13 and the detector 110 shown in FIG. 1, and may also include the image processor 120 in order to read out the X-ray images from the detector 110. Of course, a component which is configured to match respective qualities of the read out X-ray images and/or to generate a stereoscopic image may be implemented in the display apparatus 200. Such distribution of functions may be determined based on a selection of one of ordinary skill in the art to which the exemplary embodiment pertains. However, hereinafter, it is assumed that the imaging apparatus 100 includes all of the X-ray generators 11, 12, and 13, the detector 110, and the image processor 120, and the image processor 120 performs most functions which are related to X-ray imaging.

Referring to FIG. 3, according to an exemplary embodiment, the imaging apparatus 100 may be configured in such a way that the X-ray generator 10 which includes the first X-ray generator 11 and at least a second X-ray generator, that is, the second X-ray generator 12 and/or the third X-ray generator 13, is installed at an upper portion of the imaging apparatus 100, and each of the first X-ray generator 11, the second X-ray generator 12, and the third X-ray generator 13 emits X-rays in a downward direction. A detector which is configured to detect emitted X-rays is fixed to a central portion of the imaging apparatus 100. A support plate 101 on which the target object is to be placed in order to be supported is installed in the imaging apparatus 100. In addition, a compressor 102 is installed above the support plate 101 and is moveable in upward and downward directions so as to compress the target object, such as, for example, a breast, in order to increase a surface area of the breast toward which X-rays may be emitted.

Hereinafter, an overall structure and elements of an X-ray imaging apparatus according to an exemplary embodiment will be described with reference to FIGS. 4 to 9.

Figure 4:
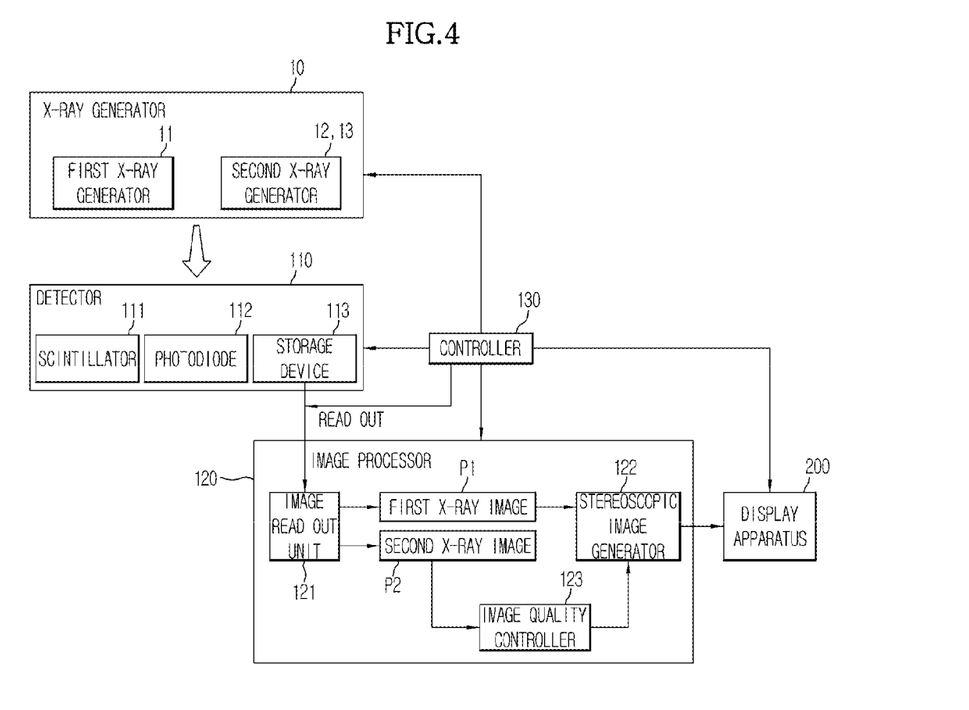
FIG. 4 is a diagram of an overall structure of an X-ray imaging apparatus, according to an exemplary embodiment.

FIG. 4 is a diagram of an overall structure of an X-ray imaging apparatus, according to an exemplary embodiment.

As shown in FIG. 4, according to an exemplary embodiment, the X-ray imaging apparatus may include the X-ray generator 10, which includes the first X-ray generator 11 and at least a second X-ray generator, that is, the second X-ray generator 12; the detector 110 which is configured to receive X-rays which are emitted from the X-ray generator 10, convert the received X-rays into electrical signals, and store the electrical signals; the image processor 120 which is configured to read out images from the X-rays that are converted into the electrical signals by the detector 110 and to perform an image processing process on the images; the display apparatus 200 which is configured to display the images that are read out or read out and image-processed by the image processor 120 to a user, and a controller 130 which is configured to control the X-ray generator 10, the detector 110, and the image processor 120.

The X-ray generator 10 generates X-rays and irradiates the target object ob with the X-rays. As described above, because the X-ray generator 10 includes the first X-ray generator 11 and the second X-ray generator 12, the X-ray generator 10 may emit a plurality of X-rays toward the target object ob so as to capture X-ray images of the target object ob at a plurality of positions.

In particular, the first X-ray generator 11 may emit first X-rays toward the target object ob such that the X-ray imaging apparatus may acquire a first X-ray image via the detector 110 and the image processor 120.

In addition, the second X-ray generator 12 (and, if present, the third X-ray generator 13) may emit second X-rays toward the target object ob in a direction that is not parallel to that of the first X-ray generator 11, that is, at an emission angle which differs from an angle at which the first X-ray generator 11 emits the first X-rays by a difference angle δ such that the X-ray imaging apparatus may acquire at least a second X-ray image via the detector 110 and the image processor 120. In this aspect, each of the second X-ray generator 12 and the third X-ray generator 13 irradiates the target object at a different angle from that of the first X-ray generator 11 in order to acquire the at least second X-ray image.

Accordingly, an X-ray generation system according to an exemplary embodiment may acquire different X-ray images, that is, the first X-ray image and at least a second X-ray image, by using a plurality of X-ray generators, that is, the first, second, and third X-ray generators 11, 12, and 13. However, a difference angle δ between emission angles of the first X-ray generator 11 and each of the second and third X-ray generators 12 and 13 may be determined in a predetermined angle range, for example, within a range of between 0° and 10° such that the image processor 120 may generate a stereoscopic image by using the first X-ray image and the at least second X-ray image in consideration of human binocular parallax.

Figure 5:
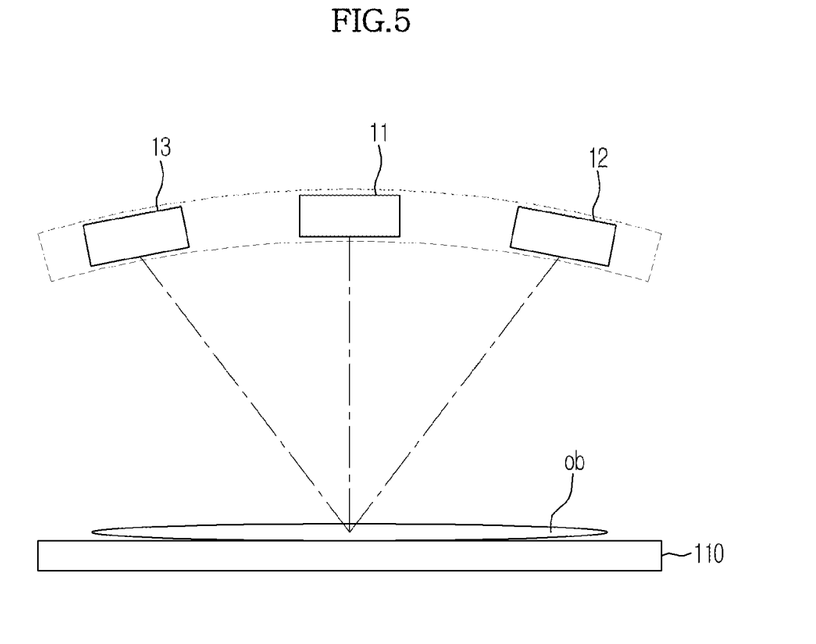
FIG. 5 is a diagram of an example of an X-ray generator of an X-ray imaging apparatus, according to an exemplary embodiment.

In some exemplary embodiments, the first X-ray generator 11, the second X-ray generator 12, and the third X-ray generator 13 may be arranged as shown in FIG. 5.

FIG. 5 is a diagram of an example of an X-ray generator of an X-ray imaging apparatus, according to an exemplary embodiment.

In particular, the first X-ray generator 11, the second X-ray generator 12, and the third X-ray generator 13 may be arranged along a curved surface having a specific curvature. In this case, the first X-ray generator 11 may be disposed in a central portion of the curved surface so as to emit X-rays toward the target object ob in a direction which is perpendicular thereto, that is, at an angle of 90° with respect to a horizontal line (and/or at an angle of 90° with respect to a flat surface of the detector 110), and each of the second X-ray generator 12 and the third X-ray generator 13 may be disposed at a respective opposite side of the first X-ray generator 11, so as to emit the first X-rays, the second X-rays, and third X-rays toward the target object ob.

FIG. 1 shows a case in which a second X-ray generator and a third X-ray generator, that is, the second and third X-ray generators 12 and 13, are used. However, as shown in each of FIG. 4 and FIG. 6, the X-ray imaging apparatus may include only one additional X-ray generator other than the first X-ray generator 11, that is, the second X-ray generator 12. As necessary, in some exemplary embodiments, for example, as shown in FIG. 5, the X-ray imaging apparatus may include two additional X-ray generators, or may include three or more additional X-ray generators.

When too many additional X-ray generators are present, it takes a long time to perform to read out an X-ray image and perform an X-ray imaging operation by using the additional X-ray generators. However, when a separate component which is configured to reduce a time required for performing the X-ray imaging operation or for reading out the X-ray image is present, such as, for example, in a case in which a plurality of detectors which are configured to detect X-rays emitted from the additional X-ray generators is provided which plurality numerically corresponds to the number of the additional X-ray generators, or in a case in which a separate storage medium which is configured to store a plurality of electrical signals which correspond to a plurality of X-rays is provided, more additional X-ray generators may be used.

According to an exemplary embodiment of the present invention, dosages of X-rays which are emitted from the first and at least second X-ray generators 11, 12, and 13 are not necessarily the same. In particular, according to an exemplary embodiment, when the X-ray imaging apparatus, such as a computed tomography (CT) scanner or FFDM apparatus, irradiates the human body with X-rays, the first X-ray generator 11 may emit X-rays at a dosage level which is set for X-ray imaging with respect to a conventional FFDM apparatus. However, the second and third X-ray generators 12 and 13 among the first, second, and third X-ray generators 11, 12, and 13 may emit X-rays toward the target object ob at a lower radiation dosage level than that of the first X-ray generator 11 in order to minimize radiation exposure to the human body.

A radiation dose, or dosage level, refers to a degree by which a target object ob is irradiated with radiation and/or to a magnitude or amount of radiation which is emitted by the respective X-ray generator.

When radiation propagates through the human body or the like, the human body absorbs energy of the radiation, thereby causing an ionization phenomenon therein. During this process, damage to deoxyribonucleic acid (DNA) of chromosomes occurs, which results in a negative health impact. In this case, once a radiation dose is greater than a dose which corresponds to a predetermined threshold dosage level, the human body is more influenced by the amount by which the radiation dose exceeds the threshold dosage level. In some cases, a target object, for example, organs of the human body, may be severely threatened, possibly even with potentially fatal consequences, because the excessive radiation dose can cause a negative health impact, such as, for example, cancer.

In this regard, when radiation dosage levels of the second and/or third X-ray generators 12 and 13 and the first X-ray generator 11 are equal, the human body is exposed to two or three times more radiation than in a conventional X-ray imaging apparatus. Thus, when the second and/or third X-ray generators 12 and 13 and the first X-ray generator 11 emit X-rays with the same high dose, the possibility of a negative influence on the human body is not excluded. Accordingly, the second and/or third X-ray generators 12 and 13 may emit radiation toward the target object ob at a low dosage level so as to minimize a corresponding increase in radiation exposure to the human body.

Conversely, when the second and/or third X-ray generators 12 and 13 emit X-rays toward the target object ob at a dosage level which is too low, it is not easy to acquire a sufficiently sharp and detailed X-ray image of the target object ob for diagnosis, and even if a predetermined level of X-ray image is acquired, the quality of the X-ray image is inevitably different from that of the first X-ray image acquired via the first X-ray generator 11. Thus, although the second and/or third X-ray generators 12 and 13 emit X-rays at a low dosage level, the second and/or third X-ray generators 12 and 13 should emit X-rays at a predetermined minimum dosage level so as to acquire an image which has at least a predetermined level of quality. In addition, it is necessary to separately image-process the second X-ray image, which is acquired by using the second and/or third X-rays of the second and/or third X-ray generators 12 and 13, by using information which relates to the first X-ray image which is acquired by using the first X-ray generator 11.

Such an image processing process is performed by the image processor 120 that will be described below. In particular, the image processor 120 performs a predetermined image processing process on read out images and also reads out images from electrical signals which are received from the detector 110.

In some exemplary embodiments, referring to FIG. 4, the first or second X-rays emitted from the first X-ray generator 11 or the second X-ray generator 12 pass or reach the detector 110 without propagating through the target object. The detector 110 converts the first X-rays and the second X-rays in order to store respective electrical signals corresponding thereto.

Hereinafter, a detector of an X-ray imaging apparatus according to an exemplary embodiment will be described with reference to FIGS. 4 and 6.

Figure 6:
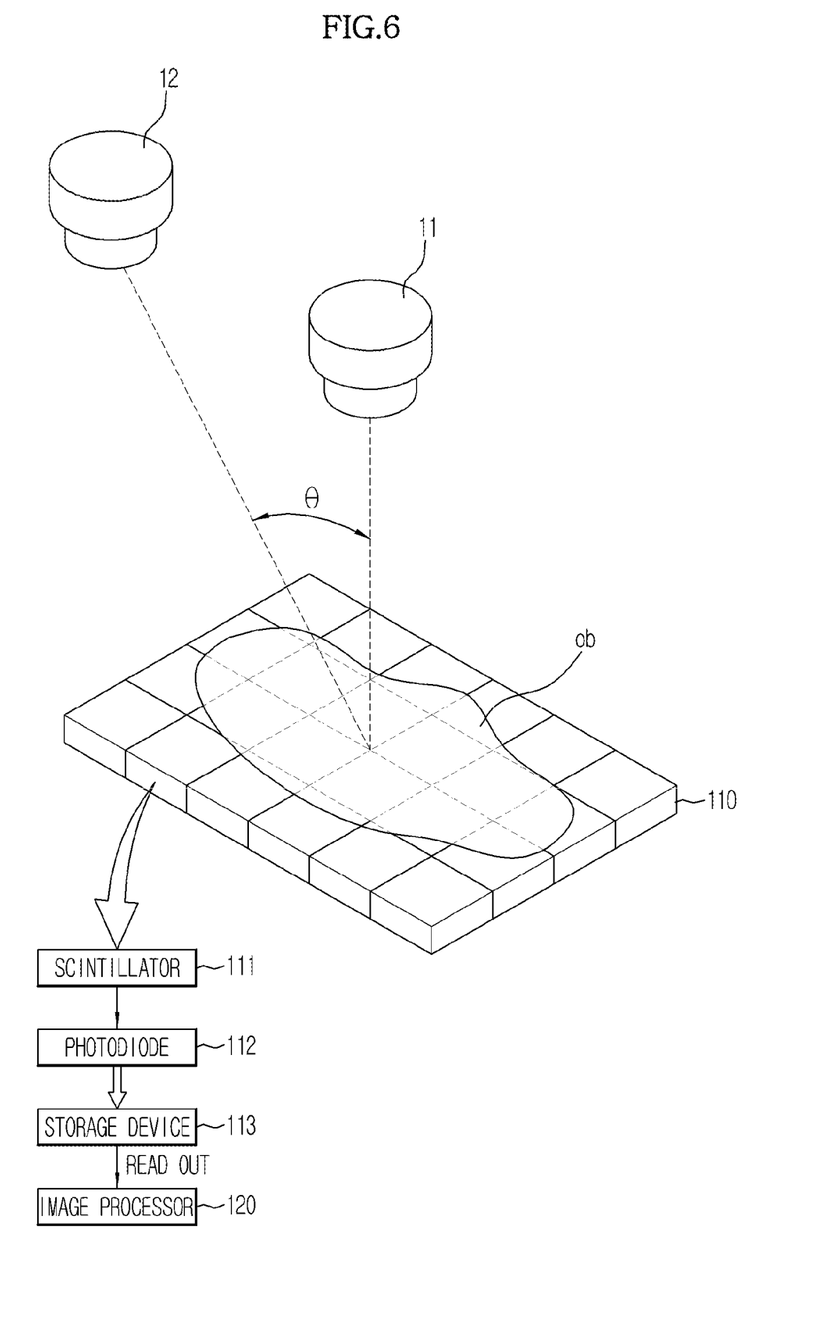
FIG. 6 is a diagram which illustrates a detector of an X-ray imaging apparatus, according to an exemplary embodiment.

FIG. 6 is a diagram which illustrates the detector 110 of an X-ray imaging apparatus, according to an exemplary embodiment.

According to an exemplary embodiment, as shown in FIGS. 4 and 6, the detector 110 may include a plurality of pixels which are configured to receive X-rays, and each pixel may include a scintillator 111, a photodiode 112, and a storage device 113.

The scintillator 111 is made up of materials that emit light when X-rays are incident thereupon, and receives X-rays which are emitted from the X-ray generators 11, 12, and 13 in order to emit light, that is, photons. Then, the photodiode 112 collects the photons and converts the photons into electrical signals. The electrical signals are stored in the storage device 113, which may be embodied as, for example, a storage capacitor or the like, such that the detector 110 finally detects X-rays. The image processor 120 reads out electrical signals which correspond to the emitted X-rays, and which are stored in the storage device 113, in order to generate an X-ray image which corresponds to incident X-rays based on the electrical signals.

A process of generating X-ray images which are captured at various angles according to an exemplary embodiment will now be described. First, the first X-ray generator 11 emits the first X-rays toward the detector 110, and the detector 110 converts the first X-rays into electrical signals and stores the electrical signals using the scintillator 111, the photodiode 112, and the storage device 113, as described above. In addition, the electrical signals are read out by the image processor 120, in particular, by an image read out unit 121 of the image processor 120, in order to generate the first X-ray image. After the first X-ray image is generated, the second and/or third X-ray generator 12 or 13 emits the second and/or third X-rays toward the detector 110 in order to generate the at least second X-ray image by performing the same process. In particular, plural X-ray images which respectively correspond to emission angles of the X-ray generators 11, 12, and 13 are sequentially generated by emitting X-rays from the X-ray generators 11, 12, and 13 at the emission angles.

Hereinafter, an image processing process of a plurality of X-ray images will be described with reference to FIGS. 4 and 7.

Figure 7:
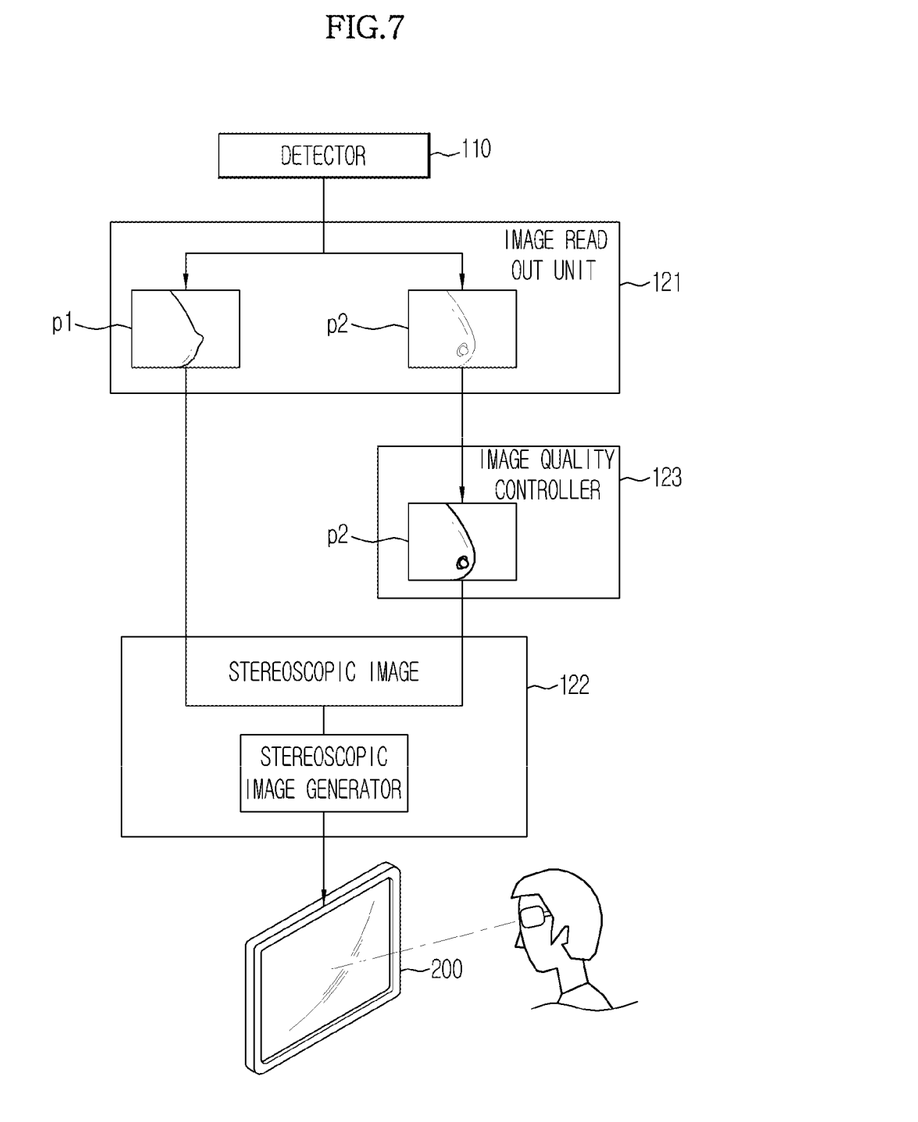
FIG. 7 is a diagram which illustrates an image processor of an X-ray imaging apparatus, according to an exemplary embodiment.

FIG. 7 is a diagram which illustrates the image processor 120 of an X-ray imaging apparatus, according to an exemplary embodiment.

Referring to FIGS. 4 and 7, according to an exemplary embodiment, the image processor 120 may include the image read out unit 121, a stereoscopic image generator 122, and an image quality controller 123.

According to an exemplary embodiment, the image read out unit 121 reads electrical signals which are stored in the storage device 113 of the detector 110 in order to read out and generate an X-ray image which corresponds to emitted X-rays, and stores the X-ray image. Thus, the first X-ray image p1 and/or the second X-ray image p2, which respectively correspond to the first X-rays and/or the second X-rays, are generated by the image read out unit 121. As shown in FIG. 7, each of the first X-ray image p1 and the second X-ray image p2 may include respective images of a target object, captured at different angles by using a difference between the first X-ray generator 11 and the at least second X-ray generator 12. Referring also to FIG. 6, the angular difference between the X-ray generator 11 and the at least second X-ray generator 12 may be equal to an angle θ.

According to an exemplary embodiment, the stereoscopic image generator 122 may generate a separate stereoscopic image by using the read out images, in particular, the first X-ray image p1 and the at least second X-ray image p2, or may control a predetermined display apparatus to display the first X-ray image p1 and the second X-ray image p2 such that a user may view the stereoscopic image of the target object ob.

The stereoscopic image generator 122 performs an image processing process and/or controls an image display such that the user may view the stereoscopic image by using the first X-ray image p1 and the second X-ray image p2. Accordingly, the user may stereoscopically view a two-dimensional (2D) image by using binocular parallax.

For example, the stereoscopic image generator 122 may perform a predetermined image processing process on the first X-ray image p1 and the second X-ray image p2 such that the first and second X-ray images p1 and p2 are used as a left eye image and a right eye image, respectively, in order to generate the stereoscopic image. Alternatively, the stereoscopic image generator 122 may control an image display of the display apparatus 200 such that the user may stereoscopically view an image.

In this case, according to an exemplary embodiment, when the stereoscopic image generator 122 performs a predetermined image processing process on the first and second X-ray images p1 and p2, the stereoscopic image generator 122 may be controlled to match respective base lines or centers of the first X-ray image p1 and second X-ray image p2 such that the user may view a stereoscopic X-ray image of the target object ob.

In detail, an example of a process of generating a stereoscopic image by the stereoscopic image generator 122 will now be described. Colors of the first X-ray image p1 and the second X-ray image p2 may be corrected into, for example, red and green by a color filter, and then, the first X-ray image p1 and the second X-ray image p2 are overlapped to generate a new combination image p3, or the corrected images are displayed on a screen.

When the first X-ray image p1 and second X-ray image p2 which are being displayed on one screen are viewed via anaglyph glasses, the target object ob of the first X-ray image p1 and second X-ray image p2 are stereoscopically viewed.

The stereoscopic image generator 122 may perform a predetermined image processing process on the first X-ray image p1 and the second X-ray image p2 so as to facilitate viewing of the stereoscopic image by using at least one of a polarized glass method and a shutter glass method. In addition, the stereoscopic image generator 122 may be controlled to repeatedly display image-processed images such that the user may view the stereoscopic image via polarized glasses or the like.

Figure 8:
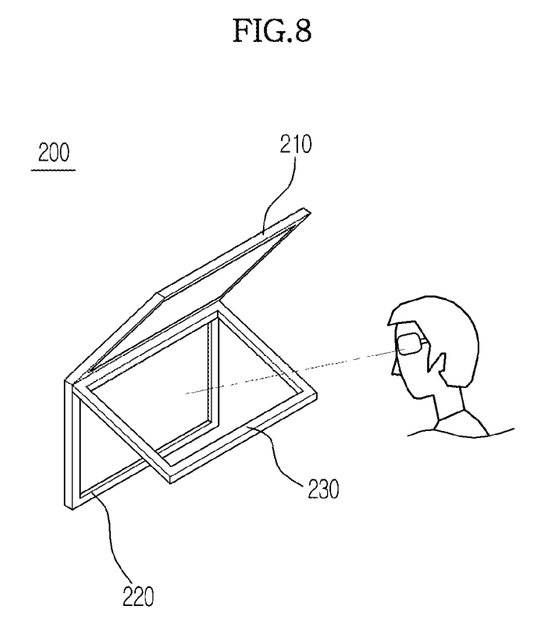
FIG. 8 is an image of a display apparatus of an X-ray imaging apparatus, according to an exemplary embodiment.
Figure 9:
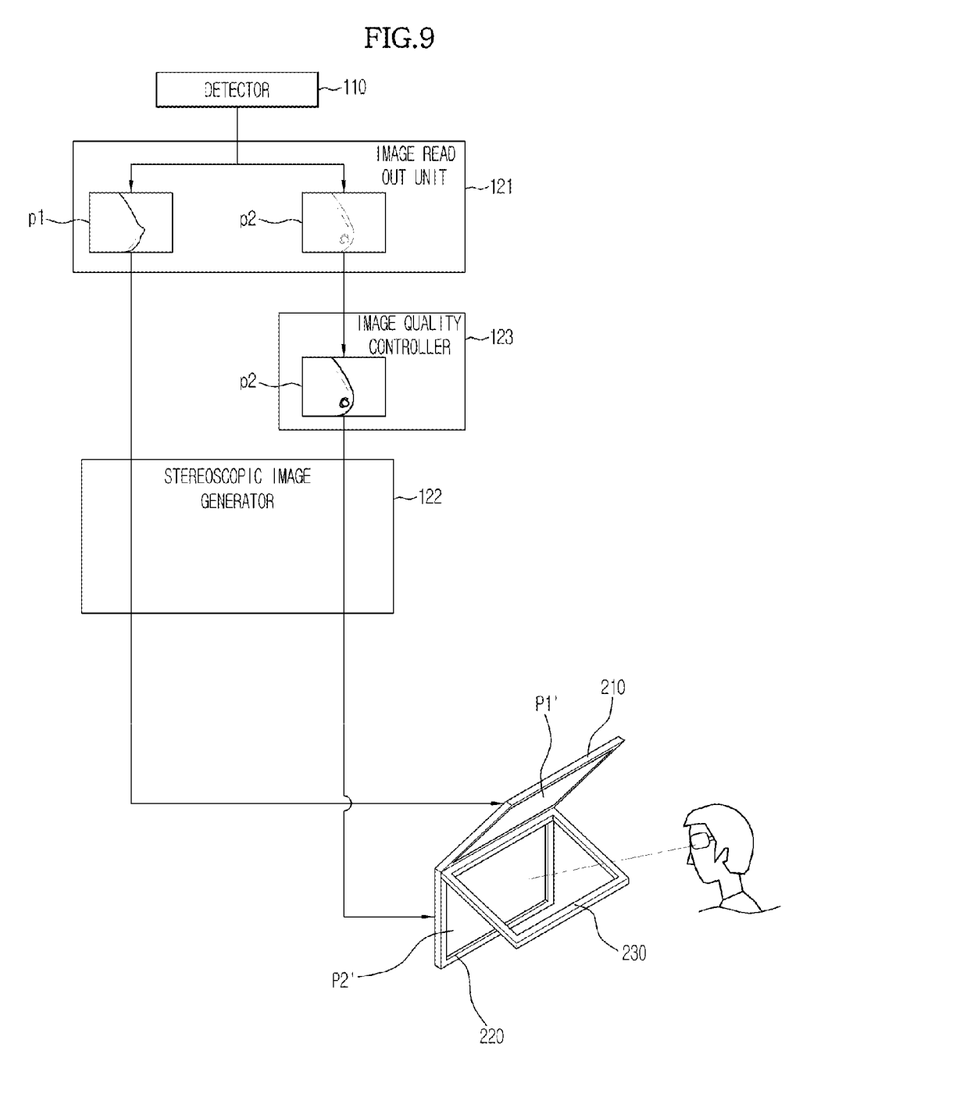
FIG. 9 is a diagram which illustrates an image processor of an X-ray imaging apparatus, according to another exemplary embodiment.

According to another exemplary embodiment, the first X-ray image p1 and the second X-ray image p2 may be displayed on the display apparatus 200 as shown in FIGS. 8 and 9 such that a doctor, a diagnostician, or the like may view the stereoscopic image.

FIG. 8 is an image of the display apparatus 200 of an X-ray imaging apparatus according to an exemplary embodiment, and FIG. 9 is a diagram which illustrates an image processor of an X-ray imaging apparatus according to another exemplary embodiment.

As shown in FIG. 8, according to an exemplary embodiment of the present invention, the display apparatus 200 includes a first display 210 which is installed at an upper portion thereof and inclined toward a front side, and a second display 220 which is installed at a lower end portion of the first display 210 in an almost perpendicular direction with respect to the ground and which includes a display monitor formed on a front surface thereof.

In addition, the display apparatus 200 further includes a third display 230 that is positioned between the first display 210 and the second display 220, and receives light, that is, images which are emitted from the first display 210 and the second display 220, and reflects and transmits the images by and through a translucent panel such that an image displayed on the first display 210 and second display 220 may be stereoscopically viewed. In particular, the third display 230 displays an image, which is obtainable by overlapping the first and second displays 210 and 220 by a predetermined degree, to a user by using a half mirror method.

As shown in FIG. 9, the stereoscopic image generator 122 may control the first display 210 and the second display 220 to respectively display the first X-ray image p1 and the second X-ray image p2. Then, the third display 230 displays the first X-ray image p1 and the second X-ray image p2 that are respectively displayed on the first and second displays 210 and 220, to the user by using a half mirror method. In this case, when the user wears predetermined stereoscopic glasses and views the first X-ray image p1 and the second X-ray image p2 that are overlapped and displayed on the third display 230, the user may stereoscopically view the first X-ray image p1 and the second X-ray image p2, and thus, may stereoscopically observe a target object, for example, the breasts. Thus, by this technique, it is easier to detect a lesion inside the target object, such as the human body, than by viewing a conventional 2D image.

According to an exemplary embodiment, the image processor 120 may further include an image quality controller 123.

According to the aforementioned exemplary embodiment, the first X-ray image p1 which is read out by the image read out unit 121 may be an image which is acquired by emitting the first X-rays at a same X-ray dosage level as that of a conventional apparatus, and the second X-ray image p2 may be an image which is acquired by emitting the second X-rays at a relatively low dosage level. In this case, it may be difficult to match an image quality of the first X-ray image p1 with an image quality of the second X-ray image p2, due to the different radiation doses which are respectively used in order to acquire the first X-ray image p1 and the second X-ray image p2. In this regard, when a stereoscopic image is generated by using two images which have different image qualities, a stereoscopic effect of the generated stereoscopic image may be degraded and/or a viewer may experience cybersickness. Thus, prior to a process of generating the stereoscopic image, an image processing process for performing a matching between the first X-ray image p1 and the second X-ray image p2 may be desirable and/or required.

In addition, it may also desirable and/or necessary to remove various noises which are often present in the first X-ray image p1 and the second X-ray image p2 in order to display a sharper stereoscopic image for more accurate lesion detection.

The image quality controller 123 of the image processor 120 performs such an image processing process. The image quality controller 123 may improve the image quality of the second X-ray image p2 so as to match the respective image qualities of the first X-ray image p1 and the second X-ray image p2, for example, prior to generation of the stereoscopic image. In addition, the image quality controller 123 may provide a function of removing noise which is generated during X-ray imaging.

When the image quality controller 123 matches the respective image qualities of the first X-ray image p1 and the second X-ray image p2, fatigue such as cybersickness may be reduced during viewing of the stereoscopic image with regard to a process of generating or displaying the stereoscopic image by using the first X-ray image p1 and the second X-ray image p2.

Hereinafter, a method for generating a stereoscopic image according to an exemplary embodiment will be described with reference to FIGS. 10 and 11.

Figure 10:
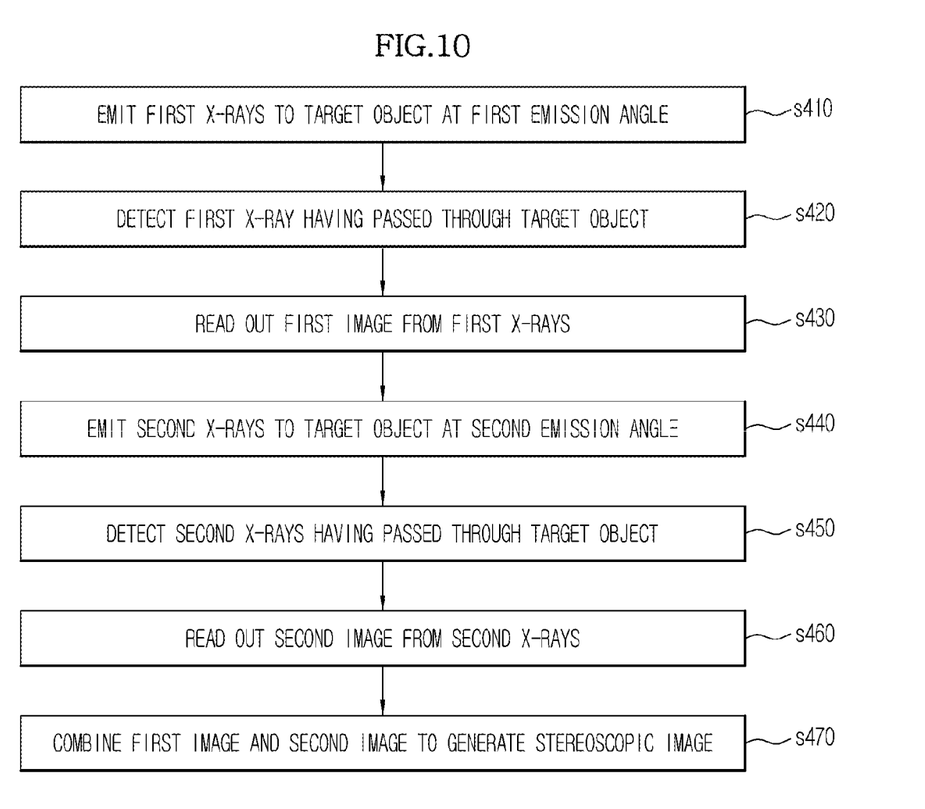
FIG. 10 is a flowchart which illustrates a method for generating a stereoscopic image, according to an exemplary embodiment.
Figure 11:
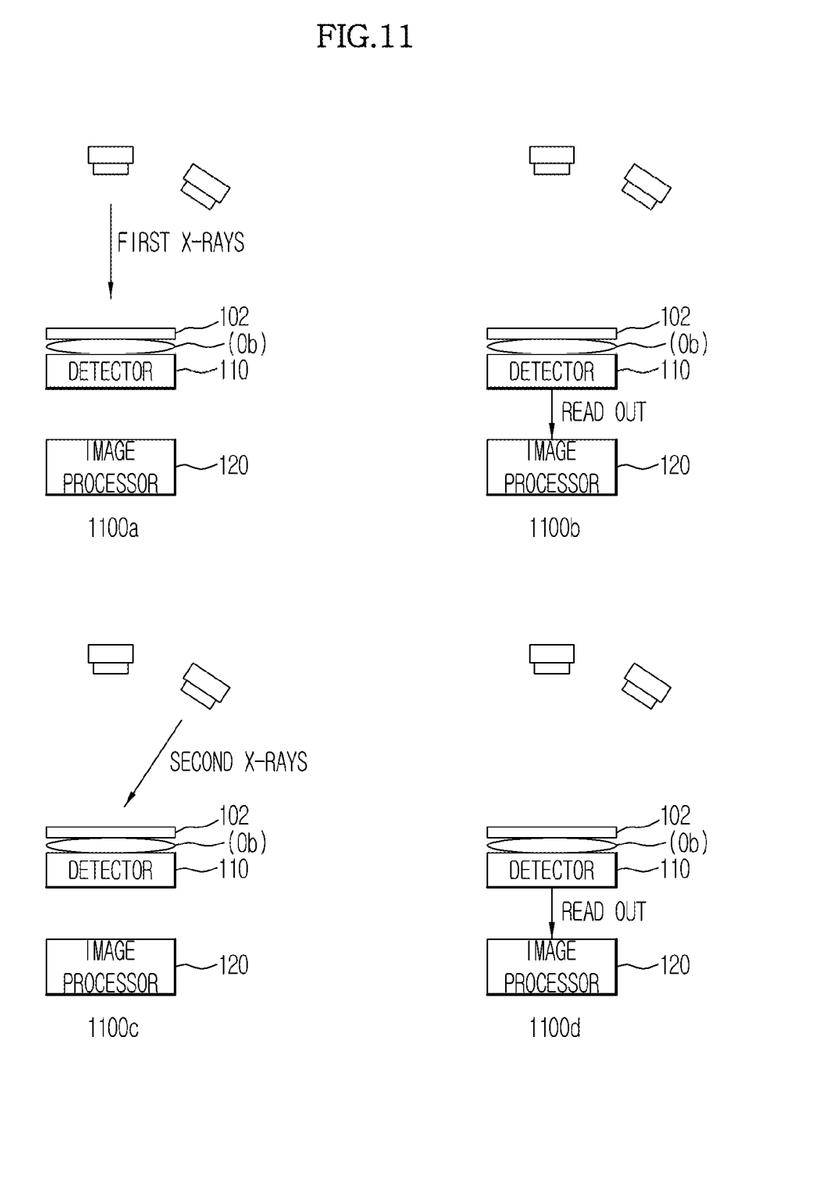
FIG. 11 is a diagram which illustrates a method for generating a stereoscopic image by using an X-ray imaging apparatus, according to an exemplary embodiment.

FIGS. 10 and 11 are a flowchart which illustrates a method for generating a stereoscopic image according to an exemplary embodiment and a diagram which illustrates the method, respectively.

As shown in FIGS. 10 and 11, according to an exemplary embodiment, in the stereoscopic image generation method, first, in operation s410 and as shown in item 1100a of FIG. 11, the first X-ray generator 11 emits the first X-rays toward the target object ob at a first emission angle. Then, in operation s420, the detector 110 detects the first X-rays which have propagated through the target object ob, converts the first X-rays into electrical signals, and stores the electrical signals by using the scintillator 111, the photodiode 112, and the storage device 113. Then, in operation s430 and as shown in itm 1100b of FIG. 11, the image read out unit 121 of the image processor 120 reads out the electrical signals from the storage device 113 and converts the electrical signals into an image in order to read out the first X-ray image p1 from the first X-rays.

Then, in operation s440 and as shown in item 1100c of FIG. 11, the second X-ray generator 12 emits the second X-rays toward the target object at a second emission angle. Then, in operation s450, similarly as described above, the detector 110 detects the second X-rays which have propagated through the target object and stores the second X-rays in the storage device 113. In operation s460 and as shown in item 1100d of FIG. 11, the image read out unit 121 of the image processor 120 reads out the second X-ray image p2 from the second X-rays.

As a result of such processes, the X-ray imaging apparatus acquires the first X-ray image p1 and the second X-ray image p2.

Then, the image quality controller 123 of the image processor 120 performs an image processing process on at least one of the first X-ray image p1 and the second X-ray image p2 in order to match the image quality of the first X-ray image p1 with the image quality of the second X-ray image p2.

After the first X-ray image p1 and the second X-ray image p2 are image processed, in operation s470, the stereoscopic image generator 122 of the image processor 120 combines the first X-ray image p1 and the second X-ray image p2 together in order to generate a new combination image, and displays the new combination image on the display apparatus 200, or controls a display of the first X-ray image p1 and the second X-ray image p2 such that a user may stereoscopically view the first X-ray image p1 and the second X-ray image p2, for example, when wearing stereoscopic glasses.

Thus, as a result, the user, such as, for example, a doctor or diagnostician, may stereoscopically view an image of a target object, for example, inner tissues of the breasts, so as to easily detect and recognize tissues which are hidden by other tissues inside the target object, and thus, the user may more quickly and accurately determine the presence or position of a lesion.

As is apparent from the above description, an X-ray imaging apparatus and a method for generating a stereoscopic image according to exemplary embodiments may enable a user to easily detect and recognize tissues which are hidden by other overlapped tissues due to high density thereof when checking, detecting, or diagnosing inner tissues of the human body by using the X-ray imaging apparatus, and to check a depth at which inner tissues of the target object are present by using image information.

In addition, a three-dimensional (3D) stereoscopic image is provided to the user such that the user may quickly and accurately check and recognize the target object, such as, for example, an inner part of the human body, with the naked eye.

As a result, according to one or more exemplary embodiments, the efficiency and accuracy of various image diagnostic processes which are implemented by using an X-ray diagnosis apparatus, a mammography apparatus, or the like may be increased.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An X-ray imaging apparatus comprising:
 a X-ray generator which is configured to emit first X-rays toward a target object at a first emission angle and to emit second X-rays toward the target object at a second emission angle which is different from the first emission angle, wherein a dosage level of the second X-rays is lower than a dosage level of the first X-rays;
 a detector which is configured to detect the first X-rays and the second X-rays;
 an image processor which is configured to acquire a first X-ray image from the detected first X-rays and to acquire a second X-ray image from the detected second X-rays, of which the dosage level is lower than the dosage level of the first X-rays, and to generate a stereoscopic image by combining the acquired first X-ray image and the acquired second X-ray image; and
 a display which is configured to display the generated stereoscopic image, wherein the image processor is further configured to match an image quality of the first X-ray image with an image quality of the second X-ray image by improving the image quality of the second X-ray image.

2. The X-ray imaging apparatus according to claim 1, wherein the image processor is further configured to improve the image quality of the second X-ray image by using information of the first X-ray image.

3. The X-ray imaging apparatus according to claim 1, wherein the image processor is further configured to match an image quality of the first X-ray image with an image quality of the second X-ray image prior to generating the stereoscopic image.

4. The X-ray imaging apparatus according to claim 1, further comprising a basic image controller which is configured to display the first X-ray image on a first screen and to display the second X-ray image on a second screen.

5. The X-ray imaging apparatus according to claim 1, wherein a difference angle δ between the first emission angle and the second emission angle satisfies 0<δ≤10°.

6. An X-ray imaging apparatus comprising:
an X-ray generator which is configured to emit first X-rays toward a target object at a first emission angle and to emit second X-rays toward the target object at a second emission angle which is different from the first emission angle, wherein a dosage level of the second X-rays is lower than a dosage level of the first X-rays;
a detector which is configured to detect the first X-rays and the second X-rays;
an image processor which is configured to acquire a first X-ray image from the detected first X-rays and to acquire a second X-ray image from the detected second X-rays of which the dosage level is lower than the dosage level of the first X-rays; and
a display apparatus comprising a first display which is configured to display the acquired first X-ray image, a second display which is configured to display the acquired second X-ray image, and a third display which is configured to receive light beams which respectively correspond to the first and second X-ray images and to display a stereoscopic image which is based on the first X-ray image and the second X-ray image and which is generated by using a half mirror method,
wherein the image processor is further configured to match an image quality of the first X-ray image with an image quality of the second X-ray image by improving the image quality of the second X-ray image.

7. The X-ray imaging apparatus according to claim 6, wherein the image processor is further configured to improve the image quality of the second X-ray image by using information of the first X-ray image.

8. The X-ray imaging apparatus according to claim 6, wherein the image processor is further configured to match an image quality of the first X-ray image with an image quality of the second X-ray image prior to the generation of the stereoscopic image.

9. The X-ray imaging apparatus according to claim 6, wherein a difference angle δ between the first emission angle and the second emission angle satisfies 0<δ≤10°.

10. A method for generating a stereoscopic image by using an X-ray imaging apparatus, the method comprising:
emitting first X-rays toward a target object at a first emission angle;
detecting the first X-rays which have propagated through the target object in order to acquire a first X-ray image;
emitting second X-rays toward the target object at a second emission angle which is different from the first emission angle, wherein a dosage level of the second X-rays is lower than a dosage level of the first X-rays;
detecting the second X-rays in order to acquire a second X-ray image;
matching an image quality of the first X-ray image with an image quality of the second X-ray image by improving the image quality of the second X-ray image; and
generating a stereoscopic image by using the first X-ray image and the second X-ray image.

11. The method according to claim 10, wherein the improving the image quality of the second X-ray image comprises:
improving the image quality of the second X-ray image by using information of the first X-ray image.

12. The method according to claim 10, wherein the matching an image quality of the first X-ray image with an image quality of the second X-ray image is performed prior to the generating the stereoscopic image.

13. The method according to claim 10, further comprising simultaneously displaying the first X-ray image, the second X-ray image, and the stereoscopic image.

14. The method according to claim 10, wherein a difference angle δ between the first emission angle and the second emission angle satisfies 0<δ≤10°.

15. The method according to claim 10, wherein the generating the stereoscopic image comprises using the first X-ray image as a left eye image and using the least second X-ray image as a right eye image.

16. The method according to claim 10, wherein the generating the stereoscopic image comprises applying a first color filter to the first X-ray image, applying a second color filter to the second X-ray image, and overlapping the first X-ray image and the second X-ray image in order to generate a combination image.

17. The method according to claim 10, wherein the generating the stereoscopic image comprises using a polarized glass technique with respect to the first X-ray image and the second X-ray image.

18. The method according to claim 10, wherein the generating the stereoscopic image comprises repeatedly displaying each of the first X-ray image and the second X-ray image at a respective predetermined interval such that the displaying is synchronized with shutter glasses to be used by a viewer.

19. The method according to claim 10, wherein the generating the stereoscopic image comprises applying a half mirror technique with respect to each of the first X-ray image and the second X-ray image.

* * * * *